(12) United States Patent
Notte et al.

(10) Patent No.: US 8,802,891 B2
(45) Date of Patent: Aug. 12, 2014

(54) PROCESS FOR THE MANUFACTURE OF ALKYLAMINO ALKYLENE PHOSPHONIC ACIDS

(75) Inventors: Patrick P. B. Notte, Wavre (BE); Jan H. J. Van Bree, Ottenburg (BE); Albert Devaux, Mont-Saint-Guibert (BE)

(73) Assignee: Italmatch Chemicals SpA, Genoa (IT)

( * ) Notice: Subject to any disclaimer, the term of this patent is extended or adjusted under 35 U.S.C. 154(b) by 1371 days.

(21) Appl. No.: 12/518,663

(22) PCT Filed: Dec. 11, 2007

(86) PCT No.: PCT/EP2007/063682
§ 371 (c)(1),
(2), (4) Date: Mar. 11, 2010

(87) PCT Pub. No.: WO2008/071689
PCT Pub. Date: Jun. 19, 2008

(65) Prior Publication Data
US 2010/0174110 A1 Jul. 8, 2010

(30) Foreign Application Priority Data
Dec. 11, 2006 (EP) .................... 06025514

(51) Int. Cl.
*C07F 9/22* (2006.01)

(52) U.S. Cl.
USPC ........................................ 562/14

(58) Field of Classification Search
USPC ........................................... 562/14
See application file for complete search history.

(56) References Cited

U.S. PATENT DOCUMENTS

| 4,260,738 A | * | 4/1981 | Tessler ............... 536/49 |
| 4,330,487 A | | 5/1982 | Redmore et al. |
| 4,707,306 A | * | 11/1987 | Leighton et al. ........... 562/14 |

FOREIGN PATENT DOCUMENTS

| DE | 3128755 | * | 2/1983 | ............. B03D 1/014 |
| EP | 0070534 | | 1/1983 | |
| GB | 2306465 | * | 5/1997 | ............. C02F 5/14 |
| WO | WO00/18695 | * | 1/2000 | ............. C25D 11/08 |

OTHER PUBLICATIONS

S. Ege, "Nucleophilic Substitution and Elimination Reactions" in Organic Chemistry, 4th Edition, p. 228, Houghton Mifflin (1999).*

* cited by examiner

*Primary Examiner* — Fereydoun G Sajjadi
*Assistant Examiner* — Kofi Adzamli
(74) *Attorney, Agent, or Firm* — Samuel Digirolamo; Husch Blackwell LLP

(57) ABSTRACT

A process for the manufacture of alkylamino alkylene phosphonic acids is disclosed. In detail, a specific phosphonate is reacted with an agent selected to yield an alkylamino moiety substituted by a radical selected from OH, OR', NH2, NHR', N(R')$_2$, NH, N, S, S—S and SH in aqueous alkaline medium having a pH of 8 or higher at a temperature of 0° C. or higher.

8 Claims, No Drawings

PROCESS FOR THE MANUFACTURE OF ALKYLAMINO ALKYLENE PHOSPHONIC ACIDS

CROSS REFERENCE TO RELATED APPLICATIONS

This application is a U.S. National Phase Application of International Application PCT Application No. PCT/EP2007/063682 filed on Dec. 11, 2007, which claims the benefit of priority from European Patent Application No. EP 06025514.8 filed on Dec. 11, 2006. The disclosures of International Application PCT Application No. PCT/EP2007/063682 and European Patent Application No. EP 06025514.8 are incorporated herein by reference.

This invention concerns a process for the manufacture of alkylamino alkylene phosphonic acids wherein the aminoalkyl moiety is substituted by a radical selected from OH, OR', N, NH, $NH_2$, NHR', $N(R')_2$, S, HS, and S—S. To that effect, a specific phosphonate starting reagent is reacted with the precursor of the selected radical in aqueous alkaline medium having a pH of 8 or higher at a temperature of 0° C. or higher.

Alkylamino alkylene phosphonic acids are well known and have found application in reducing scale formation in aqueous systems broadly, in particular in oil field operations in which the formation water, which is usually discharged with the oil at the well head, contains frequently high concentrations of alkaline earth metal and consequently exhibits high scale formation potential. GB 2 306 465 describes a method of treating water to inhibit barium scale deposition by adding a threshold level of an inhibitor mixture containing about equal parts of an alkanolamino bis(alkylene phosphonic acid) and intermolecular cyclic phosphonate which has been shown to be ineffective for scale inhibition purposes in aqueous medium. The mixture of the alkanolamine bis(alkylene phosphonic acid), having scale control properties, and the inert, in relation to scale control, intermolecular cyclic phosphonate are prepared in a typical manner by reacting the requisite starting materials, namely formaldehyde, phosphorous acid and a hydroxyalkylamine or a hydroxyalkyl alkyleneamine in the presence of a mineral acid catalyst. WO 2000/0018695 discloses a method for converting mixtures of the closed (inactive) phosphonates and open (active) phosphonates to ring-opened bis(methylene phosphonates) by submitting the mixture to a prolonged boiling treatment at a high pH equal to or higher than 12.

U.S. Pat. No. 4,330,487 describes a process of preparing N,N'-disubstituted methylene phosphonic acids by reacting α,ω-alkylene diamines with formaldehyde and phosphorous acid in aqueous medium in accordance with the Mannich reaction at a pH of generally less than 1. Zaitsev V. N. et al., Russian Chemical Bulletin, (1999), 48(12), 2315-2320, divulges modified silicas containing aminophosphonic acids covalently bonded onto the silica surface.

DE 31 287 55 discloses 3-alkoxypropyleneimino bis(methylene phosphonic acids) wherein the alkyl moiety can contain from 2 to 20 carbon atoms, a process for the manufacture of the phosphonic acid compounds and the use thereof in the flotation of non-sulfide ores. The compounds are produced by reacting an alkoxypropylene amine with formaldehyde and phosphorous acid at a reaction mixture pH below 4, more suitably below 2 in order to obtain optimum results. Suitable acidifying agents include hydrochloric acid, hydrobromic acid, sulfuric acid, phosphoric acid and sulfonic acids.

U.S. Pat. No. 3,974,090 describes iminoalkylimino phosphonates and a method for the preparation thereof. To that effect, phosphorous acid, formaldehyde and an amine are reacted in an acid medium in a conventional manner. U.S. Pat. No. 4,477,390 discloses aminomethylene phosphonic acid solutions prepared and stabilized under acid conditions. The triamine tetra(methylene phosphonic acid) compound is formed in a level of 2%. Yoshiro Yokoyama, Bull. Chem. Soc. Jpn., 58, 3271-3276 (1985), pertains to chelating phosphonate resins, prepared in a conventional manner, under acid conditions. U.S. Pat. No. 3,705,005 pertains to aminoalkylene phosphonate derivatives such as bis(aminoethyl) sulphide tetra(methylene phosphonic acid). The latter compound is prepared in acid medium in a fairly conventional manner. U.S. Pat. No. 4,234,511 relates to aminoalkylene phosphonates such as e.g. the formation of N,N(dimethylamino)-bis(phosphonomethyl)propylamine hydrochloride starting from dimethylamino propylamine. Sulfur containing methylene phosphonic acids are known from Razumovskii N. O et al., Deposited Doc. (1984), (VINITI 1784-84), 8 pp.

Significant R&D efforts expanded have not yielded remedy to prior art manufacturing shortcomings. As an example, di-phosphonate scale inhibitors do not offer, at least in part due to the presence of excessive levels of substantially inert, with respect to scale control, phosphonates such as cyclic phosphonates, a viable approach for effective commercial practice.

It is a main object of this invention to provide a process for the manufacture of alkylamino, particularly poly(alkylene phosphonic acids), preferably bis(alkylene phosphonic acids), containing substantially reduced levels of inert, in relation to e.g. water treatment, reaction products. It is another object of this invention to provide improved, substantially one-step, manufacturing technology for selected alkylene phosphonic acids without the occurrence of undue by-product negatives. Still another object of this invention aims at streamlining the phosphonic acid manufacturing technology by requiring a simplified sequence e.g. without a need for time-consuming corrective hydrolysing steps. Still another aim of the technology herein seeks to generate highly active water treatment agents, such as e.g. can be useful in relation to scale control broadly. Still another object of the invention aims at providing a simplified arrangement for synthesizing phosphonate derivatives.

The foregoing and other objectives can now be met by means of a manufacturing arrangement, as set forth in more detail below, by reacting, in aqueous medium having a substantially alkaline pH, a specifically defined reactive phosphonate with a non-phosphonate reactant.

The term "percent" or "%" as used throughout this application stands, unless defined differently, for "percent by weight" or "% by weight". The terms "phosphonic acid" and "phosphonate" are also used interchangeably depending, of course, upon medium prevailing alkalinity/acidity conditions.

A process for the beneficial manufacture of alkylene phosphonic acids has now been discovered. In more detail, the inventive arrangement aims at the preparation of phosphonic acids having the formula:

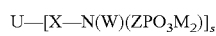

by reacting a phosphonic acid compound having the formula:

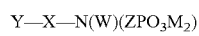

with a precursor of the moiety:
U
the structural elements having the following meaning:
Y is selected from substituents the conjugated acid of which has a pKa equal to or smaller than 4.0;

X is selected from $C_2$-$C_{50}$ linear, branched, cyclic or aromatic hydrocarbon chain, optionally substituted by a $C_1$-$C_{12}$ linear, branched, cyclic, or aromatic group, (which chain and/or which group can be) optionally substituted by OH, COOH, F, OR', $R^2O[A-O]_x$— wherein $R^2$ is a $C_1$-$C_{50}$ linear, branched, cyclic or aromatic hydrocarbon chain and SR' moieties, wherein R' is a $C_1$-$C_{50}$ linear, branched, cyclic or aromatic hydrocarbon chain, optionally substituted by $C_1$-$C_{12}$ linear, branched, cyclic or aromatic hydrocarbon groups, (said chains and/or groups can be) optionally substituted by COOH, OH, F, OR', SR' and $[A-O]_x$-A wherein A is a $C_2$-$C_9$ linear, branched, cyclic or aromatic hydrocarbon chain and x is an integer from 1 to 200;

Z is a $C_1$-$C_6$ alkylene chain;

M is selected from H and $C_1$-$C_{20}$ linear, branched, cyclic or aromatic hydrocarbon chains;

W is selected from H, $ZPO_3M_2$ and $[V—N(K)]_nK$, wherein V is selected from: a $C_2$-$C_{50}$ linear, branched, cyclic or aromatic hydrocarbon chain, optionally substituted by $C_1$-$C_{12}$ linear, branched, cyclic or aromatic groups, (which chains and/or groups can be) optionally substituted by OH, COOH, F, OR', $R^2O[A-O]_x$— wherein $R^2$ is a $C_1$-$C_{50}$ linear, branched, cyclic or aromatic hydrocarbon chain, or SR' moieties; and from $[A-O]_x$-A wherein A is a $C_2$-$C_9$ linear, branched, cyclic or aromatic hydrocarbon chain and x is an integer from 1 to 200;

K is $ZPO_3M_2$ or H and n is an integer from 0 to 200; and

U is a moiety selected from $NH_2$, NHR', $N(R')_2$, NH, N, OH, OR', S, HS and S—S wherein R' is as defined above;

s is 1 in the event U stands for $NH_2$, NHR', $N(R')_2$, OR', HS or OH; s is 2 in the event U stands for NH, S or S—S; and s is 3 in the event U stands for N;

in aqueous medium, having a pH of 8 or more, at a temperature of 0° C. or higher.

Y in the phosphonate starting compound represents a substituent the conjugated acid of which has a pKa equal to or smaller than 4.0, preferably equal to or smaller than 1.0.

The pKa value is a well known variable which can be expressed as follows:

$$pKa = -\log_{10} Ka.$$

wherein Ka represents the thermodynamic equilibrium acidity constant. The pKa values of all acid substances are known from the literature or can, if this were needed, be determined conveniently. Values are listed, e.g., in the Handbook of Chemistry and Physics.

Y can preferably be selected from Cl, Br, I, $HSO_4$, $NO_3$, $CH_3SO_3$ and p-toluene sulfonate and mixtures thereof.

In the definition of X, $R^2$, R', A and V the $C_x$-$C_y$ linear or branched hydrocarbon chain is preferably a linear or branched alkane-diyl with a respective chain length. Cyclic hydrocarbon chain is preferably $C_3$-$C_{10}$-cycloalkane-diyl. Aromatic hydrocarbon chain is preferably $C_6$-$C_{12}$-arene-diyl. When the foregoing hydrocarbon chains are substituted, it is preferably with linear or branched alkyl of a respective chain length, $C_3$-$C_{10}$-cycloalkyl, or $C_6$-$C_{12}$-aryl. All these groups can be further substituted with the groups listed with the respective symbols.

More and particularly preferred chain lengths for alkane moieties are listed with the specific symbols. A cyclic moiety is more preferred a cyclohexane moiety, in case of cyclohexane-diyl in particular a cyclohexane-1,4-diyl moiety. An aromatic moiety is preferably phenylene or phenyl as the case may be, for phenylene 1,4-phenylene is particularly preferred.

The individual moieties in the phosphonate reaction partner can, in a preferred manner, be beneficially selected from species as follows:

| Moiety | Preferred | Most Preferred |
|---|---|---|
| X | $C_2$-$C_{30}$ | $C_2$-$C_{12}$ |
|   | $[A-O]_x$-A | $[A-O]_x$-A |
| V | $C_2$-$C_{30}$ | $C_2$-$C_{12}$ |
|   | $[A-O]_x$-A | $[A-O]_x$-A | wherein for both, X and V independently:

| | | |
|---|---|---|
| A | $C_2$-$C_6$ | $C_2$-$C_4$ |
| x | 1-100 | 1-100 |
| Z | $C_1$-$C_3$ | $C_1$ |
| M | H, $C_1$-$C_6$ | H, $C_1$-$C_4$ |
| n | 1-100 | 1-25 |
| $R^2$ | $C_1$-$C_{30}$ | $C_1$-$C_{12}$ |

The U moieties can be obtained from well known precursors, readily available in the domain of the technology, which can be reacted with the reactive phosphonic acid compound. Examples of preferred precursors for the individual U moieties are as follows:

| Precursor | U Moiety |
|---|---|
| $NH_3$ | NH2 |
| $NH_2R''$ | NHR' |
| $NH_2R'$ | $N(R')2$ |
| $NH_3$ | NH |
| $NH_3$ | N |
| OH | OH |
| HOR' R'O | OR' |
| Na2S | S |
| Thiourea | SH |
| $Na_2S_2$ | S-S |

The R' substituents in the $N(R')_2$ moiety can be identical or different.

The phosphonate compounds herein can be synthesized by means of conventional measures routinely available in the relevant domain.

In one approach, the reactive phosphonate starting material and a reaction partner being a precursor of the U moiety are usually combined, in an aqueous medium, by adding stoichiometric proportions of the species, thereby taking into consideration controllable variables such as the required degree of substitution. The reaction is carried out under alkaline conditions, generally at a pH of 8 or more, preferably at a pH in the range of from 9-14. The pH is measured in the reaction medium, as is, at the reaction temperature. The reaction temperature is generally above 0° C., usually in the range of from 10° C. to 120° C. Higher reaction temperatures can be used subject to adequate pressure containment e.g. by means of standard pressure vessels.

Recovery of the reaction products is preferably carried out in a manner known per se to those skilled in the art. For example, the free phosphonic acids can be precipitated by acidification of the reaction mixture, e.g. with concentrated hydrochloric acid, filtered of, washed and dried. Further purification can, e.g., be effected by recrystallisation or chromatographic methods.

The phosphonates obtained by the process of the invention are preferably used in the chemical and pharmaceutical industry, the textile industry, the oil industry, paper industry, sugar industry, beer industry, the agrochemical industry and in agriculture.

Preferred uses are as dispersants, water treatment agents, scale inhibitors, pharmaceuticals and pharmaceutical intermediates, detergents, secondary oil recovery agents, fertilisers and micronutrients (for plants).

Examples I-XIV, which relate to the manufacturing technology of this invention, were prepared as follows.

I:

111.48 g (0.4 mole) of 96% pure 2-chloro ethyl imino bis(methylene phosphonic acid) (CEIBMPA) were mixed under stirring with 300 ml of water. 30 g of a 50% aqueous solution of sodium hydroxide (0.375 mole) was diluted with water to 100 ml and added, under stirring below 10° C., to the CEIBMPA aqueous solution. This mixture was then added over a period of 160 minutes to 162 g (2.025 moles) of 50% sodium hydroxide under good stirring at a temperature between 95° C. and 100° C. Heating was further continued for 60 minutes at 100° C. $^{31}$P NMR of the crude reaction product showed the presence of 88.3% of the hydroxy homologue of CEIBMPA; the corresponding cyclic phosphonate ester is absent from the crude product.

II:

55.74 g (0.2 mole) of 96% pure 2-chloro ethyl imino bis (methylene phosphonic acid) were mixed, under stirring at 10° C., with 75 ml of water. To this suspension was added, under stirring between 6° C. and 8° C., a solution of 15 g (0.1875 mole) of 50% sodium hydroxide diluted with water to a volume of 60 ml. This mixture was further diluted with water to a total volume of 200 ml (solution 1). 49 g (0.6125 mole) of 50% sodium hydroxide was diluted with water to a volume of 75 ml (solution 2). Solutions 1 and 2 were added to 59.11 g (1 mole) of n-propylamine, diluted in 100 ml of water, under stirring at 40° C. over a period of 70 minutes. $^{31}$P NMR of the reaction product showed the presence of 81.6% of the phosphonic acid, N-n-propyl ethylene diamine N',N'-bis(methylene phosphonic acid), 6.8% of hydroxy (ethyl bis(methylene phosphonic acid)) and 11.6% of N-n-propyl bis(ethylene diamine N',N'-bis(methylene phosphonic acid)).

III:

55.72 g (0.2 mole) of 96% pure 2-chloro ethyl imino bis (methylene phosphonic acid) were mixed, under stirring at 10° C., with 150 ml of water. To this suspension was added, under stirring between 6° C. and 8° C., a solution of 15 g (0.1875 mole) of 50% sodium hydroxide diluted with water to a volume of 50 g. This solution was added, at room temperature under stirring, to 272 g (4 moles) of a 25% ammonia solution in 120 minutes followed by heating this mixture at 95° C. for 180 minutes. $^{31}$P NMR of the reaction product showed the presence of 95% of amino ethyl imino bis(methylene phosphonic acid) and 5% of 2-hydroxyethyl imino bis(methylene phosphonic acid) (HOEIBMPA).

IV:

111.48 g (0.4 mole) of 96% pure 2-chloro ethyl imino bis(methylene phosphonic acid) were mixed, under stirring at 10° C., with 150 ml of water. To this suspension was added, under stirring between 6° C. and 8° C., a solution of 30 g (0.375 mole) of 50% sodium hydroxide diluted with water to a volume of 100 ml (solution 1). 138 g (1.725 moles) of sodium hydroxide were diluted with water to 250 ml (solution 2). Solutions 1 and 2 were added, between 6° C. and 8° C., under stirring to 13.6 g (0.2 mole) of a 25% ammonia solution in 135 minutes followed by heating the mixture at 95° C. for 240 minutes. $^{31}$P NMR of the reaction product showed the presence of 38.5% of 2-amino ethyl imino bis(methylene phosphonic acid); 32.5% of imino bis[ethyl imino bis(methylene phosphonic acid)] and 8% of the 2-hydroxy EIBMPA.

V:

111.48 g (0.4 mole) of 96% pure 2-chloro ethyl imino bis(methylene phosphonic acid) were mixed under stirring at 10° C. with 300 ml of water. To this suspension was added under stirring between 6° C. and 8° C. a solution of 30 g (0.375 mole) of 50% sodium hydroxide diluted with water to a volume of 100 ml (solution 1). 130 g (1.625 mole) of 50% sodium hydroxide were diluted with water to 250 ml (solution 2).

Solutions 1 and 2 were added, between 6° C. and 8° C. under stirring, to 54.4 g (0.8 mole) of a 25% ammonia solution in 180 minutes followed by heating the mixture between 60° C. and 80° C. for 300 minutes. $^{31}$P NMR of the reaction product showed the presence of 22% of 2-amino ethyl imino bis(methylene phosphonic acid); 56.2% of imino bis[ethyl imino bis(methylene phosphonic acid)]; 11.8% of the nitrilo tris[ethyl imino bis(methylene phosphonic acid)] and 9.8% of hydroxy EIBMPA.

VI:

55.72 g (0.2 mole) of 96% pure 2-chloro ethyl imino bis (methylene phosphonic acid) were mixed under stirring at 10° C. with 150 ml of water. To this suspension was added, under stirring between 6° C. and 8° C., a solution of 15 g (0.1875 mole) of 50% sodium hydroxide diluted with water to volume of 50 ml (solution 1). 97 g (1.2125 moles) of 50% sodium hydroxide were diluted with water to 120 ml (solution 2).

Solutions 1 and 2 were added at room temperature under stirring to 4.56 g (0.067 mole) of a 25% ammonia solution in 150 minutes followed by heating at 95° C. for 240 minutes. $^{31}$P NMR of the reaction product showed the presence of 19.9% of imino bis[ethyl imino bis(methylene phosphonic acid)]; 76.3% of nitrilo tris[ethyl imino bis(methylene phosphonic acid)] and 3.8% of hydroxy EIBMPA.

VII Comparative:

20.44 g of n-propyl ethylene diamine (0.2 mole) were mixed with 32.8 g (0.4 mole) of phosphorous acid and 59.12 g (0.6 mole) of a 37% aqueous HCl solution. The solution was heated at 107° C. under stirring and 36.10 g (0.44 mole) of a 36.6% aqueous formaldehyde solution were added in 25 minutes. Heating was continued further for 120 minutes at 107° C. $^{31}$P NMR analysis of the reaction product showed the presence of 37.2% of n-propyl ethylene diamine tri(methylene phosphonic acid); 28% of the N-n-propyl N-methylene phosphonic acid ethylene diamine; 10.6% of the N-n-propyl ethylene diamine N',N'-bis(methylene phosphonic acid) as well as 11.6% of unconverted phosphorous acid.

VIII Comparative:

Reaction of ethylene diamine with phosphorous acid, formaldehyde in the presence of HCl in accordance with D. Redmore et al. in Phosphorus and Sulfur, 1983, Vol 16, pp 233-238.

30 g (0.5 mole) of ethylene diamine were mixed with 82 g (1 mole) of phosphorous acid, 250 ml of water and 250 ml (2.69 moles) of 37% aqueous HCl. This solution was heated under stirring to 110° C. and 90.25 g (1.1 mole) of 36.6% aqueous formaldehyde solution were added in 60 minutes. Heating was continued at 110° C. for 120 minutes. $^{31}$P NMR analysis of the reaction product showed the presence of 25.2% of ethylene diamine tetra(methylene phosphonic acid); 48.4% of 2-amino ethyl imino bis(methylene phosphonic acid); 10.1% of ethylene diamine tri(methylene phosphonic acid) and 4.7% of N-methyl ethylene diamine tri(methylene phosphonic acid) as major constituents.

IX:

38.86 g (0.4 mole) of diallylamine were mixed with 200 ml of ethanol and 100 ml of water. 111.48 g (0.4 mole) of 96% pure 2-chloro ethyl imino bis(methylene phosphonic acid) were mixed with 150 g of water and 30 g (0.375 mole) of 50% sodium hydroxide itself diluted with water to a volume of 120 ml at 10° C. (Solution 1). 98 g (1.225 moles) of 50% sodium hydroxide were diluted with water to 150 ml (Solution 2).

Solutions 1 and 2 were added to the diallylamine solution under stirring at 70° C.-75° C. Heating was continued at 75° C. for 3 hours. $^{31}$P NMR analysis of the reaction product showed 63% of diallylamine mono-ethyl 2-imino bis(methylene phosphonic acid) and 10% of 2-hydroxy ethyl imino bis(methylene phosphonic acid).

X:

58.66 g (0.2 mole) of 96% pure 3-chloro propyl imino bis(methylene phosphonic acid) were mixed under stirring at 10° C. with 100 ml of water. To this suspension was added under stirring between 6° C. and 8° C. a solution of 32 g (0.4 mole) of 50% sodium hydroxide diluted with water to a volume of 100 ml. 18.8 g (0.2 mole) of phenol were mixed with 100 ml of water and 32 g (0.4 mole) of 50% aqueous sodium hydroxide. This solution was added to the 3-chloro propyl imino bis(methylene phosphonic acid) solution at 8° C. 24 g (0.3 mole) of 50% sodium hydroxide diluted with water to 50 ml were further added to the reaction mixture at 8° C. and the resulting mixture was heated at 100° C. for 6 hours. At room temperature, 80 ml of concentrated hydrochloric acid were added which resulted in the formation of a white precipitate collected by filtration. After washing and drying a white powder (44.08 g or 65% yield) was obtained. $^{31}$P NMR of this product showed 98% of the 3-phenoxy propyl bis (methylene phosphonic acid).

XI:

26.41 g (0.2 mole) of sodium sulfide trihydrate were dissolved in 70 ml of water. 58.65 g (0.2 mole) of 96% pure 3-chloro propyl imino bis(methylene phosphonic acid) were mixed with 100 ml of water and 16 g (0.2 mole) of 50% sodium hydroxide at 10° C. under stirring (Solution 1). 44 g (0.55 mole) of 50% sodium hydroxide were diluted with water to a volume of 70 ml (Solution 2). Solutions 1 and 2 were added to the sodium sulfide solution with good stirring at 70° C. and heating was extended for 3 hours after complete addition. $^{31}$P NMR analysis of the reaction product showed 89% of the di[propyl 3-imino bis(methylene phosphonic acid]sulfide and 11% of the corresponding thiol.

XII:

26.41 g (0.2 mole) of sodium sulfide trihydrate were dissolved in 70 ml of water. 55.7 g (0.2 mole) of 2-chloro ethyl imino bis(methylene phosphonic acid) were mixed with 75 ml of water and 15 g (0.1875 mole) of 50% sodium hydroxide at 10° C. under stirring (Solution 1). 49 g (0.6125 mole) of 50% sodium hydroxide were diluted with water to a volume of 100 ml (Solution 2). Solutions 1 and 2 were added to the sodium sulfide solution with good stirring at 10° C. The reaction mixture was then heated under stirring at 80° C. for 4 hours. $^{31}$P NMR analysis of the reaction product showed 88% of the di[ethyl 2-imino bis(methylene phosphonic acid)]sulfide and 12% of the corresponding 2-hydroxy ethyl imino bis(methylene phosphonic acid).

XIII:

58.66 g (0.2 mole) of 96% pure 3-chloro propyl imino bis(methylene phosphonic acid) were mixed under stirring at 10° C. with 100 ml of water. To this suspension was added under stirring at 10° C. a solution of 16 g (0.2 mole) of 50% sodium hydroxide diluted with water to a volume of 60 ml (Solution 1). A sodium disulfide solution was prepared from 26.41 g (0.2 mole) of sodium sulfide trihydrate mixed under stirring with 6.4 g (0.2 mole) of sulfur in 100 ml of water till complete sulfur dissolution. 44 g (0.55 mole) of 50% sodium hydroxide were diluted with water to a volume of 70 ml (Solution 2). Solutions 1 and 2 were added to the disulfide solution under stirring at room temperature followed by heating at 95° C. for 3 hours. $^{31}$P NMR of the reaction mixture showed 58% of the di[propyl imino bis(methylene phosphonic acid)]disulfide; 20% of the corresponding mono-sulfide and 9% of the hydroxy propyl imino bis(methylene phosphonic acid).

XIV:

58.66 g (0.2 mole) of 96% pure 3-chloro propyl imino bis(methylene phosphonic acid) were mixed under stirring at 10° C. with 100 ml of water. To this suspension was added under stirring at 10° C. a solution of 32 g (0.4 mole) of 50% sodium hydroxide diluted with water to a volume of 100 ml (Solution 1). 15.22 g (0.2 mole) of thiourea were mixed with 50 ml of water (Solution 2). Solution 2 was added to solution 1 under stirring at 10° C. After completion of the addition 16 g (0.2 mole) of 50% sodium hydroxide diluted with water to a volume of 60 ml were added at 10° C. under stirring. The reaction mixture was heated at 95° C. for 7 hours. 32 g (0.4 mole) of 50% sodium hydroxide were then added at room temperature and the reaction mixture heated at 100° C. under stirring for 2 hours. $^{31}$P NMR of the reaction mixture showed 53% of propyl imino bis(methylene phosphonic acid) sodium thiolate; 17% of di[propyl imino bis(methylene phosphonic acid)]sulfide and 16% of hydroxy propyl imino bis(methylene phosphonic acid).

These testing data confirm the major benefits attached to the inventive technology as compared to the prevailing state of the art. In particular: Example I shows that, contrary to the GB 2 306 465 arrangement, the inventive technology yields a reaction product substantially devoid of cyclic phosphonates which are ineffective for e.g. water treatment applications. Example II of the invention vs. comparative Example VII highlights the selectivity towards desirable species such as n-propyl amine ethyl imino bis(methylene phosphonic acid): Ex. II—81.6%, Ex. VII—10.6%. Example III of the invention yields 95% of amino ethyl imino bis(methylene phosphonic acid) as compared to 48.4% of the same compound in comparative Example VIII. Example IV shows the formation of 38.5% of an amino compound together with 32.5% of a compound having the primary amine fully methylene phosphonated while preserving the unsubstituted secondary amino group. Such mixtures could not be synthesized by known methods. The observations formulated in relation to Example IV are equally applicable to Example V yielding 56.2% of a compound carrying an unreacted secondary amine and a fully methylene phosphonated primary amine. This product could not be prepared, to any meaningful extent, by means of conventional methods. In this respect, Examples 1-34 of U.S. Pat. No. 4,477,390 illustrate the formation, in levels of 2%, vs. 56.2% in Example V of this invention, of the unreacted secondary amine. The inventive data are equally unexpected in comparison to the testing data of U.S. Pat. No. 3,974,090. Example II of the '090 patent highlights the predominant conversion to completely phosphonated species as compared to 56.2% of an unreacted secondary amine in Example V of this invention. Along the same lines, Example VI of this invention shows the formation of 76.3% of the aminotrisphosphonic compound as compared to 49% in accordance with Example I of the '090 art. In addition, the inventive technology allows the easy grafting of derivatives as compared to the cumbersome approaches of the art starting from presynthesized amines.

Example IX illustrates the possibility of preparing, with high yields, a bis(methylene phosphonic acid)ethylene diamine whereby the second nitrogen carries two allyl (R') substituents. Using traditional technology, this synthesis would require starting from N,N-di(allyl)ethylene diamine which is difficult and expensive to so prepare. Examples X through XIV concern the syntheses of various derivatives in high yields. Comparable to Example IX, these methods demonstrate the versatility of the claimed method vs. what can be made starting from art established linear approaches.

The invention claimed is:

1. A process for the manufacture of alkylamino alkylene phosphonic acids having the formula:

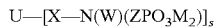

by reacting a phosphonic acid compound having the formula:

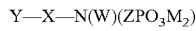

with a precursor of the moiety:
U the structural elements having the following meaning:

Y is selected from: substituents the conjugated acid of which have a pKa equal to or smaller than 4.0;

X is selected from $C_2$-$C_{50}$ linear, branched, cyclic or aromatic hydrocarbon chains, optionally substituted by a $C_1$-$C_{12}$ linear, branched, cyclic, or aromatic group, (which chain and/or which group can be) optionally substituted by OH, COOH, F, OR', $R^2O[AO]_x$ wherein $R^2$ is a $C_1$-$C_{50}$ linear, branched, cyclic or aromatic hydrocarbon chain, and SR' moieties, wherein R' is a $C_1$-$C_{50}$ linear, branched, cyclic or aromatic hydrocarbon chain, optionally substituted by $C_1$-$C_{12}$ linear, branched, cyclic or aromatic hydrocarbon groups, (said chains and/or groups can be) optionally substituted by COOH, OH, F, OR' and SR'; and [A-O]$_x$-A wherein A is a $C_2$-$C_9$ linear, branched, cyclic or aromatic hydrocarbon chain and x is an integer from 1 to 200;

Z is a $C_1$-$C_6$ alkylene chain;

M is selected from H and $C_1$-$C_{20}$ linear, branched, cyclic or aromatic hydrocarbon chains;

W is selected from H, $ZPO_3M_2$ and [V—N(K)]$_n$K, wherein V is selected from: a $C_2$-$C_{50}$ linear, branched, cyclic or aromatic hydrocarbon chain, optionally substituted by $C_i$-$C_{12}$ linear, branched, cyclic or aromatic groups, (which chains and/or groups can be) optionally substituted by OH, COOH, F, OR', $R^2O[A-O]_x$— wherein $R^2$ is a $C_1$-$C_{50}$ linear, branched, cyclic or aromatic hydrocarbon chain, and SR' moieties; and from [A-O]$_x$-A wherein A is a $C_2$-$C_9$ linear, branched, cyclic or aromatic hydrocarbon chain and x is an integer from 1 to 200;

K is $ZPO_3M_2$ or H and n is an integer from 0 to 200; and

U is a moiety selected from $NH_2$, NHR', N(R')$_2$, NH, N, S, SH, and S—S wherein R' is as defined above;

s is 1 in the event U stands for $NH_2$, NHR', N(R')$_2$, or HS;
s is 2 in the event U stands for NH, S or S—S; and s is 3 in the event U stands for N;

in aqueous medium, having a pH of 8 or more, at a temperature of 0° C. or higher.

2. The process as claimed in claim 1 wherein the pH of the reaction medium is in the range of from 9-14.

3. The process as claimed in claim 1 wherein X is selected from $C_2$-$C_{30}$ or [A-O]$_x$-A wherein A is $C_2$-$C_6$ and x is from 1-100.

4. The process as claimed in claim 1 wherein the individual moieties in the phosphonate reaction partner are selected as follows: X is $C_2$-$C_{30}$ or [A-O]$_x$-A; V is $C_2$-$C_{30}$ or [A-O]$_x$-A; wherein for both, X and V independently, A is $C_2$-$C_6$ and x is 1-100; $R^2$ is $C_1$-$C_{30}$; Z is $C_1$-$C_3$; M is H or $C_1$-$C_6$; and n is 1-00.

5. The process as claimed in claim 1 wherein U is selected from: $NH_2$; NHR'; N(R')$_2$; NH; and N.

6. The process as claimed in claim 1 wherein the individual moieties in the phosphonate reaction partner are selected as follows: X is $C_2$-$C_{12}$ or [A-O]$_x$-A; V is $C_1$-$C_{12}$ or [A-O]$_x$-A; wherein for both, X and V independently, A is $C_2$-$C_4$ and x is 1-100; $R^2$ is $C_1$-$C_{12}$; Z is $C_1$; M is H or $C_1$-$C_4$ and n is 1-25.

7. The process as claimed in claim 1 wherein the precursor for U is selected from: $NH_3$; $NH_2R'$; NH(R')$_2$; Na2S; thiourea; and $Na_2S_2$.

8. The process as claimed in claim 1 wherein Y is selected from Cl, Br, I, $HSO_4$, $NO_3$, $CH_3SO_3$ and p-toluene sulfonate.

* * * * *